United States Patent
Cook et al.

(10) Patent No.: US 7,837,091 B2
(45) Date of Patent: Nov. 23, 2010

(54) LASER SYSTEM AND DELIVERY DEVICE OPERATION LOGGING METHOD AND KIT

(75) Inventors: David W. Cook, Hayward, CA (US); Ken Arnold, Soquel, CA (US)

(73) Assignee: Laserscope, San Jose, CA (US)

( * ) Notice: Subject to any disclaimer, the term of this patent is extended or adjusted under 35 U.S.C. 154(b) by 1194 days.

(21) Appl. No.: 11/419,415

(22) Filed: May 19, 2006

(65) Prior Publication Data

US 2006/0264918 A1 Nov. 23, 2006

Related U.S. Application Data

(60) Provisional application No. 60/682,945, filed on May 20, 2005.

(51) Int. Cl.
*G06F 7/00* (2006.01)
(52) U.S. Cl. ....... 235/375; 235/492
(58) Field of Classification Search .......... 235/492; 385/53
See application file for complete search history.

(56) References Cited

U.S. PATENT DOCUMENTS

| | | |
|---|---|---|
| 4,258,977 A | 3/1981 | Lukas et al. |
| 4,402,569 A | 9/1983 | Bow et al. |
| 4,519,390 A | 5/1985 | Horne |
| 4,722,337 A | 2/1988 | Losch et al. |
| 4,766,433 A | 8/1988 | Herman et al. |
| 4,919,508 A | 4/1990 | Grace et al. |
| 4,998,794 A | 3/1991 | Holzman |
| 5,016,964 A | 5/1991 | Donnelly |
| 5,134,469 A | 7/1992 | Uchimura |
| 5,142,598 A | 8/1992 | Tabone |
| 5,521,392 A | 5/1996 | Kennedy et al. |
| 5,562,717 A | 10/1996 | Tippey et al. |
| 5,623,357 A | 4/1997 | Kight et al. |
| 5,702,428 A | 12/1997 | Tippey et al. |
| 5,725,563 A | 3/1998 | Klotz |
| 5,742,718 A | 4/1998 | Harman et al. |
| 6,149,643 A | 11/2000 | Herekar et al. |
| 6,200,265 B1 | 3/2001 | Walsh et al. |
| 6,298,255 B1 | 10/2001 | Cordero et al. |

(Continued)

OTHER PUBLICATIONS

Atmel AT88SC1608, "8×2256×8 Secure Memory with Authentication," Rev. 0971E-11/99, 20pp.

*Primary Examiner*—Daniel A Hess
(74) *Attorney, Agent, or Firm*—Haynes Beffel & Wolfeld LLP

(57) ABSTRACT

A method for operating a laser system for a medical procedure, or a similar system, comprises detecting presence of a portable memory device like a smart card coupled to the laser system, and reading data on the portable memory device usable to identify an associated delivery device. An identifier is read from the associated delivery device after it is coupled to the laser. A process is executed to verify the configuration including matching the identifier read from delivery device with the delivery device associated with the portable memory device, verifying that the portable memory device includes a data structure adapted for storage of an event log, and enabling delivery of laser energy if said authenticating and said verifying are successful. A kit comprising a delivery device and a portable memory device supporting the process is provided to users of the laser system.

7 Claims, 5 Drawing Sheets

U.S. PATENT DOCUMENTS

| | | |
|---|---|---|
| 6,442,525 B1 | 8/2002 | Silverbrook et al. |
| 6,536,431 B1 | 3/2003 | Simler |
| 6,689,124 B1 | 2/2004 | Thiberg |
| 7,451,935 B2 * | 11/2008 | Chang ........................ 235/492 |
| 2005/0033619 A1 | 2/2005 | Barnes et al. |
| 2005/0177274 A1 * | 8/2005 | O'Dougherty et al. ...... 700/231 |

* cited by examiner

LASER SYSTEM AND DELIVERY DEVICE OPERATION LOGGING METHOD AND KIT

CROSS REFERENCE TO RELATED APPLICATION

The benefit of U.S. Provisional Application No. 60/682,945, filed 20 May 2005, entitled LASER SYSTEM AND DELIVERY DEVICE OPERATION LOGGING METHOD AND KIT, is hereby claimed.

BACKGROUND OF THE INVENTION

1. Field of the Invention

The present invention relates to fiber optic delivery systems and laser medical systems, and to generating accurate information concerning use of such systems.

2. Description of Related Art

It is useful to gather accurate information about the operation of medical laser systems and for use of consumable delivery devices like optical fibers, for many purposes. For example, such information can be useful in analysis of the medical procedures followed using the systems, which is needed for research about improvements to the procedures. Also, such information can be used to prevent unsafe operation of the systems, including overuse of delivery devices that can degrade with excessive use, use of delivery devices that are not intended for use with the systems, and so on.

In the prior art, smart cards and like systems have been used to verify payment for operation of the systems, to ensure that the operators are authenticated before enabling use of the systems, to ensure that the host system is being used properly. For example, U.S. Pat. No. 6,536,431 describes a system for dispensing oxygen in which smart cards are used to ensure that the user has purchased credits that allow use. The smart card can also be used for "logging details such as parameters of each session of use of the dispenser," (See, '431 patent, column 5, lines 6-17) so that the nature of use of the dispenser can be monitored over time. The logging information relates only to use of the dispenser, and the person possessing the card. U.S. Pat. No. 6,298,255 describes a "smart sensor" which includes a memory module used as a data archive for "patient and performance data." (See, '255 patent, column 6, lines 3-10). U.S. Pat. No. 6,149,643 describes a system in which a smart card is used for pre-payment for use of a laser system for vision correction. According to the '643 patent, data from procedures can be transferred to the smart card for storage (See, '643 patent, column 3, lines 55-58; and column 21, lines 10-41).

The prior art smart cards just described are not used to log information about use of a delivery device adapted for a specific laser system, sold separately from the laser system, nor verify use of a proper delivery device. Thus, such prior art systems are not suitable for ensuring use of authorized delivery devices, for ensuring safe use of delivery devices, or for gathering data about use of such devices.

In one prior art, a laser system includes a smart card reader, and software that relies on the smart card for the purposes verifying use of a correct type of delivery device, and preventing overuse of such device. In this prior art system, a "smart card" is provided in a kit including a fiber optic delivery device. The smart card is arranged to allow use of the delivery device for a single procedure. The fiber optic delivery device includes a device ID indicating the type of delivery device is read by the laser system software. The laser system software requires that a device type ID stored on the smart card in the kit, matches the device type ID of the attached delivery device and that the card is valid before allowing the system to enter an application mode.

In operation, the prior art system executes a mutual authentication protocol when the smart card is inserted into the card reader on the laser system, to determine if the laser and card are both genuine. Once the card and laser have been authenticated, memory in an unused card is stamped with the identifying data. If the card is used, when it is inserted as indicated by identifying data stored on the card, the data indicating an amount of energy use on the card is checked to insure that the prior use did not result in delivery of energy sufficient for a full procedure. This prevents unsafe reuse, while enabling insertion and removal of the card during set up or for arbitrary reasons. If the device associated with the card has been used for a procedure, the card will no longer be valid and a message will appear on the laser system indicating that the card has expired. Also, the card is invalidated and the laser system is disabled.

This process is repeated whenever the card is removed and reinserted, the fiber optic delivery device is removed and reattached, or the power is turned off and back on. Thus, the prior art system is used to ensure that an authentic kit us being used, that the proper type of delivery device is attached, and that the delivery device is not being used for more than one procedure.

U.S. Pat. No. 5,742,718 describes a fiber optic delivery device with a smart card attached to it. The '718 patent mentions that the card can be used for storing data about use of the device during procedures (See, '718 patent, column 7, lines 24-50, column 8, lines 19-60). However, there are no safeguards provided against circumvention of the data logging function in the card, so that the delivery device could be used "off record", and making the data gathering process unreliable. In order for data logging to be useful in detailed analysis, it is necessary that complete data be gathered. Without safeguards against operating the laser system and using the delivery device off record, then the prior art approaches are not satisfactory for use in important analysis and record keeping.

It is desirable to provide a system and method that improves the data gathering processes associated with laser systems and delivery devices used in medical procedures.

SUMMARY OF THE INVENTION

A method for operating a laser system is described which supports creation of event logs in a portable memory device associated with a specific delivery device, in which further includes procedures for ensuring that an accurate and complete event log is maintained. In some environments in which laser systems are utilized, such as for the performance of medical procedures, accurate and complete event logs are necessary for use as information in any follow-on research, failure analysis or other process evaluation. A technological approach to ensuring the creation of such event logs is provided, overcoming problems associated with the prior art in which unreliable and sketchy data had been gathered.

An embodiment includes operating a laser system, or other system that is adapted to be coupled with a delivery device for energy or other deliverable product, to perform a procedure that includes a sequence of events. The method for operating comprises detecting presence of a portable memory device like a smart card coupled to the system, and reading data on the portable memory device usable to identify an associated delivery device, such as a copy of the identifier on an associated delivery device;

reading an identifier for a delivery device, such as a fiber optic with the coupler having a machine-readable identifier, after it is coupled to the system;

matching the identifier read from delivery device with the associated delivery device indicated by data read from the portable memory device;

verifying that the portable memory device includes a data structure adapted for storage of an event log, comprising event codes corresponding to events in the sequence of events, by for example reading the data structure to determine that it is properly configured; and enabling delivery of a product such as laser energy to the delivery device if said matching and said verifying are successful.

Embodiments of the method include authenticating the portable delivery device as well. Embodiments of the method also include signaling an event logging error to a laser operator, or disabling the laser system, if any event code is not successfully written during the event logging process.

By providing for a combination of associating a specific delivery device with a portable memory device, authenticating the portable memory device, and verifying that the portable memory device includes a data structure adapted for storage of an event log, assurances that an accurate event log corresponding with the particular delivery device will be maintained are provided. The portable memory device can be returned to a site in which data is recovered from the device and used for analysis. The portable memory device can be returned separately from the delivery device, simplifying the procedure by avoiding the need to handle the delivery device along with the memory device after use the delivery device in a procedure.

Embodiments also include logging data concerning the condition of the system during use of the particular delivery device, such as a count of error codes, an age of the gain medium or pump energy source in a laser system, outputs of energy sensors and the like sampled during the procedure, and do on. In such systems, the process includes verifying that the portable memory device includes a data structure adapted for storing such system condition data.

A kit comprising a delivery device and a portable memory device arranged to support the process described above is also described herein. An embodiment of the kit includes a delivery device, such as a fiber optic delivery device, having a coupler adapted for optical connection to the laser system, and a machine-readable medium adapted to be read by the system that stores and identifier for the delivery device. The kit also includes a portable memory device including machine-readable memory, adapted to be written to and read by the system. The machine-readable medium includes a data structure arranged for use as an event log for storing event codes corresponding with respect to the events in the sequence of events, a data structure arranged for use as a log of the condition of the laser system during the sequence of events, and data usable by the system to verify the presence of the data structure or data structures. The portable memory device also includes other data structures and data necessary for supporting the processes described herein. By providing a kit including a delivery device and a portable memory device which are configured together, and arranged for event logging that is tied to use of the particular delivery device in the kit, the operators are able to ensure more accurate data gathering with operation of a system over a large number of procedures, with a degree of confidence not available in the prior art.

An embodiment of the technology described comprises a portable memory device arranged as described above, for use with a specific delivery device.

Other aspects and advantages of the present invention can be seen on review of the drawings, the detailed description and the claims, which follow.

DETAILED DESCRIPTION

A detailed description of embodiments of the present invention is provided with reference to the FIGS. 1-6.

Figure 1:
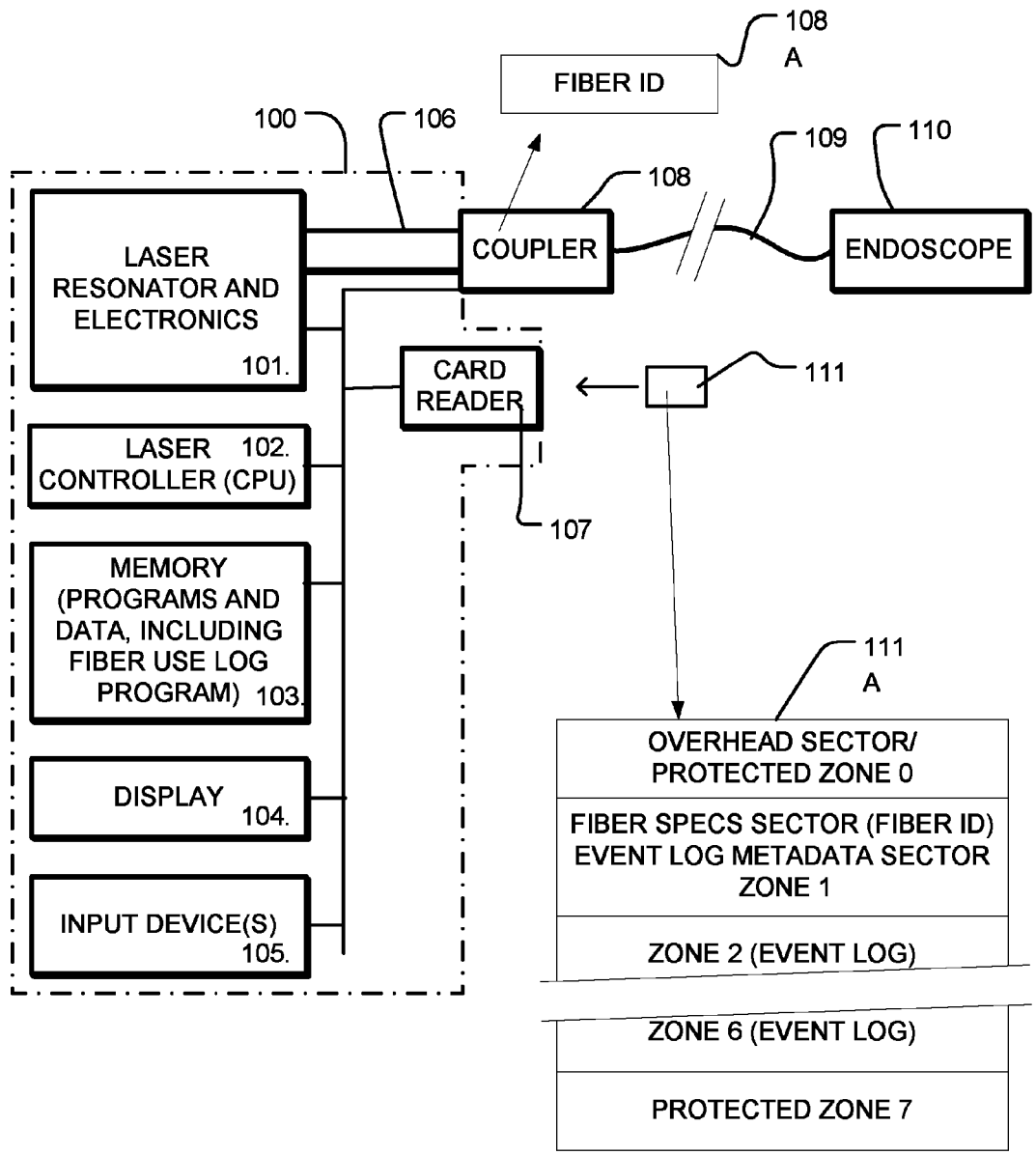
FIG. 1 is a simplified block diagram of a laser system with a fiber-optic delivery device and a smart card configured for logging events related to use of the delivery device.

FIG. 1 illustrates a medical laser system configured with an optical delivery device and a smart card that are arranged for maintaining an event log that records use of the delivery device with the laser system. The medical laser system includes a laser system 100 which includes a laser resonator and electronics 101, a laser controller 102 that comprises a data processor such as a CPU, memory 103 storing programs and data, a display 104 and user input device or devices 105. The laser system 100 also includes an optical output 106 coupled to the laser resonator and electronics 101 adapted for connection to a coupler 108 for an attached optical fiber 109, which is in turn adapted for use with an endoscope 110 or other tip-of-fiber apparatus. The medical laser system shown in the block diagram in FIG. 1 is representative of a variety of commercially available systems, such as the Green Light PV™ Laser System provided by Laserscope, Inc. of San Jose, Calif., modified by programming as described herein. Embodiments of the invention are applied to other types of systems for delivery of energy, like non-coherent light sources or other radiation sources, or other products, such as liquids and gases, which can be used in procedures, such as medical procedures, where accurate event logging can be important or useful.

In the illustrated system, the coupler 108 comprises a machine-readable memory that stores an identifier for the fiber "FIBER ID" 108A. The FIBER ID comprises a code, such as a serial number, that is usable to specifically identify the delivery device that includes the fiber 109, the coupler 108 and optionally other components. In alternative systems, the FIBER ID may comprise a code that is usable to identify the type of delivery device, so that more than one delivery device may have the same FIBER ID. Representative embodiments of the coupler 108 comprise an optical-electrical connector implemented as described in U.S. Pat. No. 4,722,337, in which the coupler comprises a plug having contact points that can be arranged to indicate the FIBER ID in electrical form readable by the laser controller 102. In other embodiments, nonvolatile memory such as EEPROM can be incorporated into, or attached to, a coupler that includes both optical and electrical connectors, and programmed in the factory with the FIBER ID. In yet other embodiments, so-called RFID technology could be incorporated into, or attached to, the delivery device. Using the RFID technology, physical electrical connectors may be unnecessary, allowing for radio frequency coupling of power into a memory device that is connected to or incorporated in the delivery device, along with radio frequency communication of the FIBER ID to the laser controller 102.

The laser system 100 includes a port for a portable memory device, where the portable memory device is adapted for storing an event log. A portable memory device is one that is adapted to be moved independent of the laser system, including like memory cards that are commercially available in a variety of configurations. In the illustrated embodiment, the port comprises the smart card reader 107 adapted to read a smart card 111. Any of a variety of commercially available smart cards can be used, which comprise an article of manufacture that includes secure memory and logic circuits used as an authentication processor, along with matching card reader 107. In other embodiments, the portable memory device comprises an element that is attached to the delivery device. In such embodiments, it may not be necessary to provide an additional component for matching the portable memory device with the identifier on the delivery device. It is desirable however, as discussed below to use a portable memory device which can be separated from the delivery device for return to a data processing center in which the event log data is analyzed.

As illustrated in FIG. 1, the smart card 111 includes memory 111A which is configured for use as an event log before delivery to an end user, and which is used by the laser system 100 to maintain a log of events that relate to use of the delivery device (108-110).

In the illustrated embodiment, the memory 111A is configured to include a plurality of storage zones (ZONE0-ZONE7), including a protected zone ZONE 0 with an OVERHEAD SECTOR. The OVERHEAD SECTOR includes a software and data structures used by the smart card in coordination with the smart card reader, to authenticate the card. In the illustrated embodiment, ZONE 1 which includes a fiber specifications sector and an event log metadata sector, and ZONE2-ZONE7 including memory space for storing the event log. A "fiber signature" is stored in the memory structure on the card, either in the protected zone, or elsewhere, which matches is a similar fiber signature on a delivery device that is provided with the card, as parts of a kit. Thus, the fiber signature in the smart card unambiguously associates the smart card with a particular delivery device, in the illustrated example. The OVERHEAD sector includes a data structure arranged for storing parameters written by software executed in the laser controller. The fiber specifications sector in ZONE 1 includes information about the delivery device usable by the laser controller for calibration, confirmation of the type of delivery device and the like. The event log metadata sector in ZONE 1 comprises configuration information to define the structure of the event log, and other parameters that are used for verifying proper operation of the delivery device associated with the card. ZONE 2 through ZONE 7 are used for storing the event log defined by the metadata according to the processes described below.

The data could be used to develop a statistical database comparing techniques. This data could be used to determine if fibers that are being returned as defective are not simply used up in normal operation. The card could also be used to record data about specific procedures.

A variety of types of data can be stored, including among other data types discussed herein, the following:
Date/time card insertion
Date/time most recent device connected
Date/time procedure started (first exposure)
Date/time procedure ended (last exposure)
Date/time most recent device removed.
Date/time card removed.
Number of device connects with subsequent exposures
Total number of exposures during a procedure
Maximum foot down time on a foot pedal used for starting and stopping an exposure
Minimum foot down time on a foot pedal used for starting and stopping an exposure
Lasing time for entire procedure
Total Joules for each fiber.
Average Power during entire procedure Recording data as events in an event log has a number of advantages, over simply recording large data files of data accumulated by the laser controller. This method has the advantage in overcoming the slow write speeds of smart cards. Instead of having to update large structures of data on the smart card, only a few bytes, typically a fixed number of bytes, need to be written to the card for each event and the pointer to that part of the card incremented by number of bytes written. The software that reads the cards and calculates the data totals from the events can then be done using a much faster microprocessor than the laser system has.

This method also has the advantage of allowing the entire procedure to be replayed in the exact same manner as it took place. Not unlike replaying a video tape.

In one embodiment, each event will record a short event code to indicate the type of event and a fixed number of bytes of additional data. For most events this additional data would be a time stamp or other data associated with that event such as the new power setting or an error number along with the time of day.

Representative events that could be recorded are listed in the following table:

| Event | Triggered when | Description | Data recorded |
|---|---|---|---|
| Standby State | going to Standby state. | Standby state is a safe system state where the shutter is closed and the lamp is idling. | System time. |
| Adjust State | going to Adjust state. | Adjust state is when the system is calibrating itself to output the correct power while the shutter is closed. | System time. |
| Pwr Adj State | completing Adjust state. | After the power adjustment is complete this event is used to record the actual power achieved. | Power setting/ real time. |

-continued

| Event | Triggered when | Description | Data recorded |
|---|---|---|---|
| Ready State | going to Ready state. | Ready state is after the power adjust and the shutter is opened and ready to do an exposure. | System time. |
| Exposure State | going to Exposure state | Exposure state occurs when the foot pedal is depressed in Ready state to initiate an exposure. | System time. |
| Card In | a fiber card is inserted into the system. | A fiber card is a smart card that is shipped with the fiber and will be used to capture the procedure data.. | Date/Time fiber card is inserted. |
| Fiber In | a fiber is attached to the system. | A fiber completes an electrical signature when attached to the system. | Date/Time fiber is attached. |
| Fiber Out | a fiber is disconnected from the system. | The fiber electrical signature is lost. | Date/Time fiber is disconnected. |
| Error | a system error occurs | The system has detected an error condition | Error #/real time |

A recycling program can be promoted which encourages users to return used cards. The data from these returned cards would then be used to read the procedure data from the used cards and store it in a database.

This database can then be used to collect statistical data on procedures, verify claims of defective fibers that are returned, and also to detect possible system misuse.

A more detailed example of the memory configuration in the smart card, or other portable memory device includes data which is protected from change during use of the smart card by a fuse, or otherwise. Such protected memory stores parameters that are provided by the memory manufacturer, parameters provided by the card manufacturer, and parameters provided by the card issuer. Parameters provided by the card issuer in this example include a fiber identifier associating the card with a specific delivery device or set of delivery devices, and other information that can be associated with the card before issuing it. Parameters provided by the memory manufacturer and the card manufacturer include authentication data, such as encryption keys, passwords and so on.

Data stored in a protected sector for an embodiment of a smart card configured for an event log as described herein, includes a structure that provides a number of parameters, including an identifier for the type of associated device, a parameter written at the start of a procedure by the laser controller indicating an amount of energy use by the laser system, a parameter indicating the date and time the card was is inserted, and the laser serial number written by the laser controller.

An example of the smart card also stores parameters identifying specifications of the delivery device, such as the fiber transmission, the diameter the fiber, the length of fiber and so on usable by the laser controller to manage energy delivery through the device. Also, parameters stored include the fiber serial number uniquely identifying the fiber, a product name and other information.

Table 1 illustrates the configuration of an example of a procedure sector that comprises metadata for the event log. The sector shown in Table 1 includes the structure FBR_SECT_PROC, includes a first page that is written once, and a second page which is updated upon every event log operation. First page includes a parameter indicating the size of the zone, a parameter indicating the software revision for the sector, and a parameter like an exposure delay time that may be specific to a laser system or vary from system to system, and a parameter indicating the date and time that the system was turned on. The exposure delay time is used to improve the accuracy of energy measurements based on signals generated during events that evoke the logging procedure, so that the amount of time between an event signaling the start of a exposure and the time at which energy is actually delivered can be used to more accurately indicate the energy delivered by measuring the time. In the page updated on every event, a number of parameters are written, including the last date and time that the card had been inserted, a total exposed Joule count, a pointer to the next event to be written, a parameter indicating the number of events recorded, a total checksum for the events, and a CRC for the structure.

TABLE 1

Procedure Sector

```
typedef struct FBR_SECT_PROC {    // Fiber Procedure Sect - no PW
        // Page 1: Written once
    CSEC    csExpDelay;   // Exposure delay time.
    CMTod   todSysOn;     // Date/time system turned on.
        // Page 2: updated every event.
    CMTod   todLast;      // Last Date/Time card was in system.
    JOULES  jlTotal;      // Total Exposed joules.
    short   nEvtPtr;      // Pointer to next event.
    short   nEvents;      // Number of events recorded.
    WORD    wCheckSum;    // Total checksum of events.
    CRC     crc;          // CRC for this struct.
} FBR_SECT_PROC1;
```

Table 2 includes a list of the event codes used for logging, and the structure of the log data. As can be seen, the structure of the log data comprises the structure PROC_EVT that includes an event code and event data. The event code is selected from the enumeration PROC_EVT_CODE. The event data comprises the data structure PROC_EVT_DAT. In the illustrated example, the event data includes the system time, a date and time, and one of the structures Exp, Adj or Err. The Exp structure provides an amount in time that the laser was in the ready state before exposure, and an exposure time. The Adj structure provides a power setting and an adjustment time. The Err structure provides an error code, and a real-time in seconds.

TABLE 2

Procedure Events

| | |
|---|---|
| PROC_EVT_NIL, | // 0 is an invalid event number |
| PROC_EVT_TO_STBY, | // SysTime on change to Standby State |
| PROC_EVT_TO_ADJ, | // SysTime on change to Adjust State |
| PROC_EVT_TO_RDY, | // SysTime on change to Ready State |
| PROC_EVT_FROM_ADJ, | // Pwr Setting on change from Adjust State/ time of day |
| PROC_EVT_FROM_EXP, | // Time on change to Ready in decisec, time of change toe Expose in decisec. |
| PROC_EVT_CARD_IN, | // Date/Time card inserted. |
| PROC_EVT_FBR_IN, | // Date/Time fiber connected. |
| PROC_EVT_FBR_OUT, | // Date/Time fiber disconnected. |
| PROC_EVT_FBR_INVALID, | // Date/Time invalid fiber connected. |
| PROC_EVT_TO_ERROR, | // Error # / Time occured. |
| PROC_EVT_START, | // Date/Time procedure started. |
| PROC_EVT_END, | // Estimated Date/Time procedure ended. |

In support of the event logging process, the laser controller 102 gathers data concerning operation of the laser, the delivery device and the card. For example, such data includes the following counters:

Fiber Card Counter—A fiber card counter in non-volatile memory is incremented every time a new fiber card is inserted and authenticated.

Device Counter—A device connect counter in non-volatile memory incremented every time a delivery device is disconnected after having a minimum amount of energy delivered to it.

Procedure Counter—A procedure counter in non-volatile memory incremented every time a period of inactivity has been exceeded and a minimum of amount of energy has been delivered to it.

In an embodiment of the portable memory device, data structures are created when the device is formatted for holding information copied from at least one of the Fiber Card Counter, Device Counter and Procedure Counter.

Figure 2:
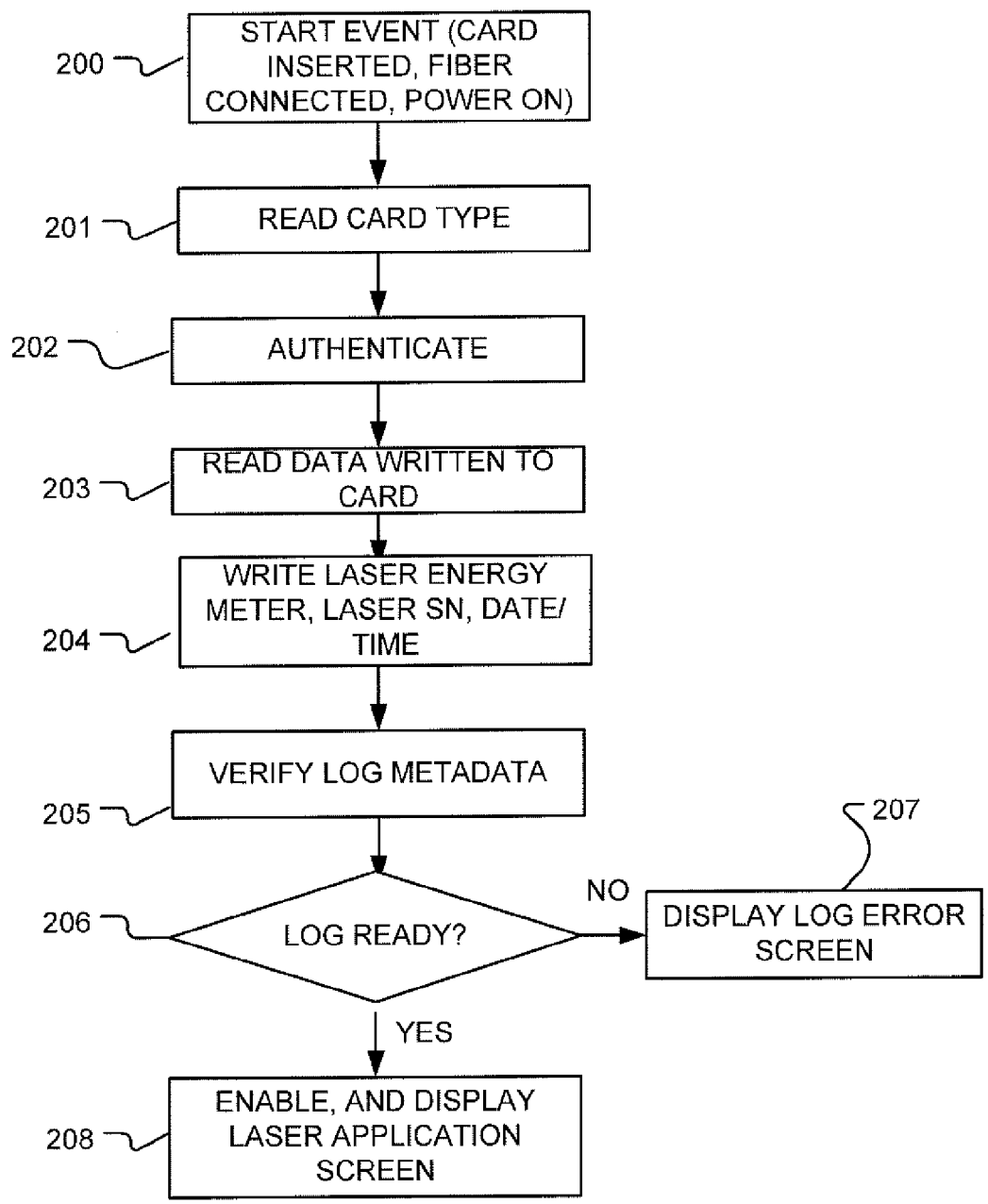
FIG. 2 is a simplified flow chart of a computer program executed by the laser controller in the system of FIG. 1, used for enabling use of the laser system for a procedure.

FIG. 2 is a flow chart illustrating the procedure executed by the laser controller 102 in response to the fiber use log program stored in the memory 103. The program is initiated on a start event, such as detection of a combination of a card inserted, a fiber connected and laser system power on (block 200). The program then reads the card type parameter at block 201. The authentication process is executed at block 202, to identify the card and verify that the card is an authorized card. Next, the program reads the parameters stored on the card at block 203. Next, the energy meter count from the laser system, the laser serial number and the date and time parameters are written to the card (block 204). In the next step, the software verifies the metadata for the event log, which is maintained in the procedure sector described above (block 205). After checking the metadata, the software ensures that the log data structure is ready for use at block 206. If the log data structure is not ready, or not present on the card, then a log error is displayed on the display device of the laser system (block 207). If the log data structure is ready at block 206, then the software enables the laser system and displays a laser application screen (block 208). In embodiments of the laser system in which it is necessary to maintain accurate event log for every procedure, or for procedures that require use of the smart card/delivery device kit, if at block 206 the log data structure is not present or ready, then after displaying the log error screen at block 207, the user is unable to enable the laser system for a procedure, without using a different delivery device and smart card kit.

As can be seen, with respect to the flow chart of FIG. 2, the laser system is enabled by detection of an authenticated card having a log data structure present and ready for use. Although not illustrated in the flow chart, other steps in the procedure must be successful to enable the laser system, such as verifying that the data read from the card is valid, and verifying that the authentication process at block 202 is successful.

Figure 3:
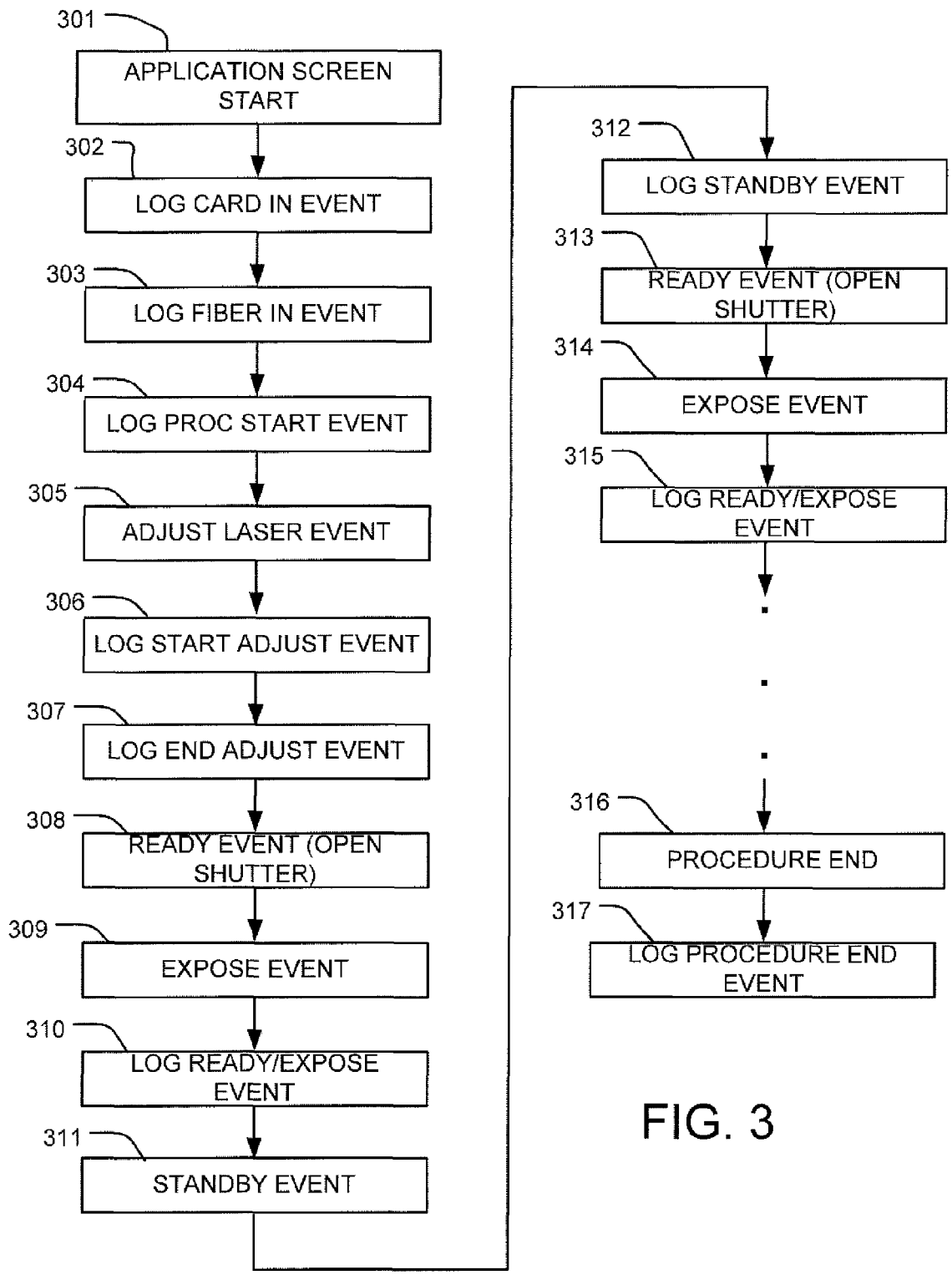
FIG. 3 is a simplified flow chart of a computer program executed by the laser controller in the system of FIG. 1, representing event logging for a procedure.

FIG. 3 illustrates a representative event logging process beginning with the application screen, which is entered at block 211 of FIG. 2. Thus, after the start of an application screen at block 301, the laser controller logs the card insert event PROC_EVT_CARD_IN (block 302). The laser controller also logs the fiber connected event PROC_EVT_FBR_IN (block 303). At this time, based on interaction with the application screen, the laser controller optionally can log the starting of a procedure PROC_EVT_START (block 304). A typical procedure includes a laser adjust state (block 305), in which the laser system performs calibration and adjusts output power according to the needs of the particular procedure and the particular delivery device. At this time, the transition to the adjust state is logged PROC_EVT_TO_ADJ (block 306). At the conclusion of the adjust state, the transition out of the adjust state is logged PROC_EVT_FROM_ADJ (block 307). Next, the laser system transitions to the ready state, according to the operation parameters of the laser system, at which time events like opening the output shutter occur in an exemplary system (block 308). The expose event, in which actual laser energy measured in Joules is delivered through the delivery device, occurs next (block 309). The ready state and the end of the expose state are logged as a single event PROC_EVT_FROM_EXP in the illustrated example (block 310). Next, in a representative procedure, the laser will transition to a standby state (block 311), such as in a pause in the procedure. The laser controller then logs the transition to standby event PROC_EVT_TO_STBY (block 312). The procedure may then include another ready event at block 313 and expose event at block 314. After the expose event, the PROC_EVT_FROM_EXP event is logged (block 315). The procedure can include a variety of events which are logged, until a procedure end at block 316. Based on interaction with the application screen or other operations which occur at the end of the procedure, the laser controller logs the procedure end event PROC_EVT_END at block 317.

Not illustrated in the flow chart is a use of the event codes PROC_EVT_START and PROC_EVT_END. The procedure start event PROC_EVT_START could be defined, for example, as the time the first exposure occurs (first PROC_EVT_FROM_EXP) or the time the system first goes into Ready state (first PROC_EVT_TO_RDY). The procedure end event PROC_EVT_END could be defined, for example, as the time that the Procedure Counter in the laser controller 102, described above, is incremented.

The procedure illustrated in FIG. 3 is representative of simpler or more complicated procedures executed using the laser system and the delivery device. Thus, procedures executed using laser system with the event logging as described herein can involve different sequences of events and logging steps. Also, other of implementations are arranged to log different types of events or different combinations of events, as suits the needs of the particular system being implemented.

In another embodiment, the events described above which relate to the use of a particular delivery device, are augmented with information about the condition of the laser system during the procedure. In such embodiments, the event log is extended or another structure is set up, to accept information such as age of the laser gain medium or pump energy source, outputs of sensors indicating performance of the laser, the number of error events recorded in an error log on the laser system, or similar information useable to assist in analysis of the procedure executed with the specific delivery device.

Figure 4:
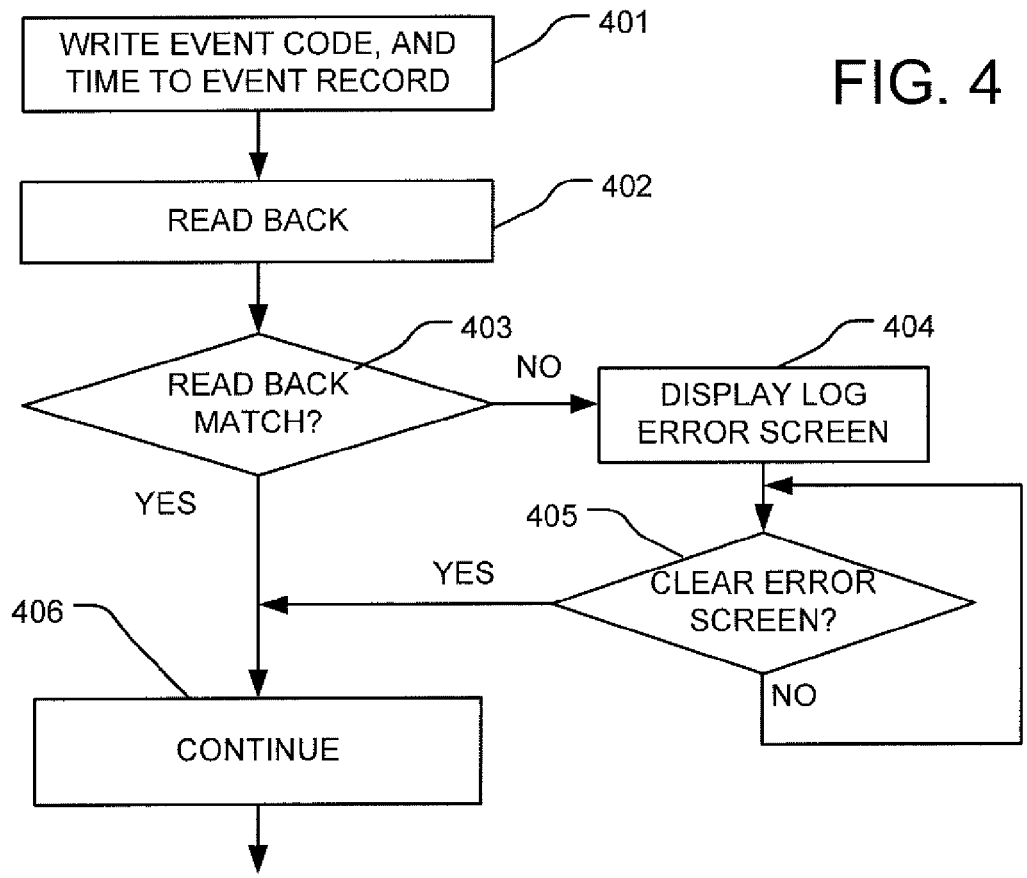
FIG. 4 is a simplified flow chart of a computer program executed by the laser controller in the system of FIG. 1, for logging data on a smart card.

FIG. 4 illustrates the event logging process used in a representative system. The event logging process begins at block 401 with the laser system writing an event code, including the time of the event, to an event record on the smart card. After writing the event code and the time, the data is read back at block 402. The laser controller determines whether the read back data matches the event code and time originally written at block 403. If the data matches, then the laser controller software continues with controlling the laser and the interactive display on the laser system according to normal operation (block 406). If at block 403, the read back data does not match, then the laser controller displays a log error screen at block 404. At step 405, the laser controller waits for an event clearing the error screen executed by the operator of the laser, such as by providing an input signal. After clearing error screen, the laser controller branches to block 406 to continue operation. In alternative embodiments, if an error is detected at block 403, the laser system can be disabled. In other embodiments, the operator may not be required to clear the error screen in order to continue with the procedure.

Figure 5:
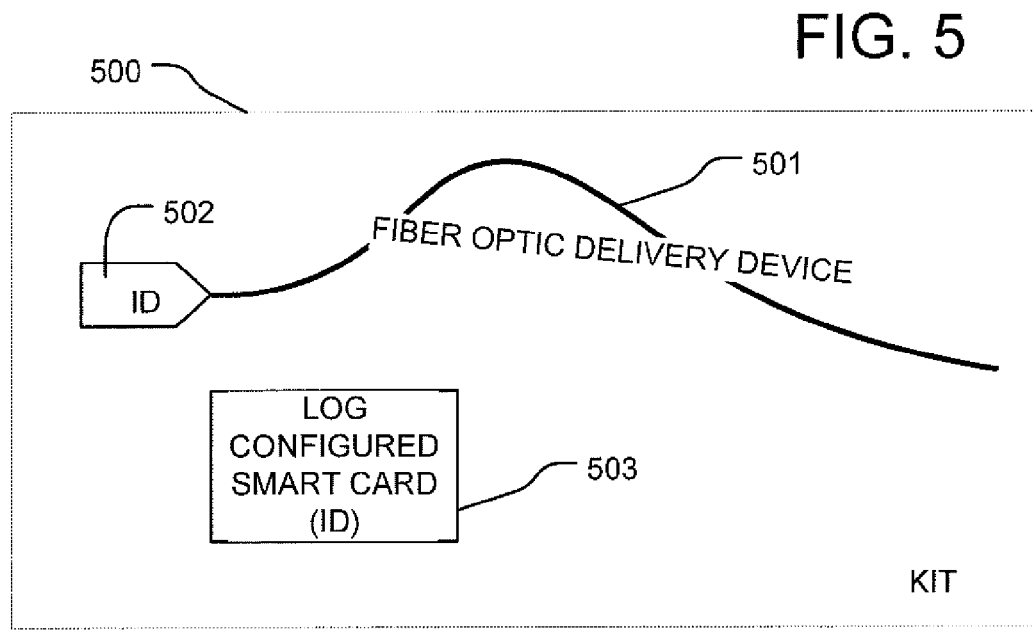
FIG. 5 illustrates a kit comprising a fiber-optic delivery device with a machine-readable identifier and a matching smart card for use with a laser system like that of FIG. 1.

FIG. 5 illustrates an embodiment of a delivery device/smart card kit 500. The kit 500 includes a delivery device that includes an optical fiber 501 and a coupler 502. The coupler 502 comprises a machine-readable identifier for the delivery device 501, as described above. The smart card 503 is configured for use in logging events that are executed using the fiber optic delivery device included with the card, as described above.

Figure 6:
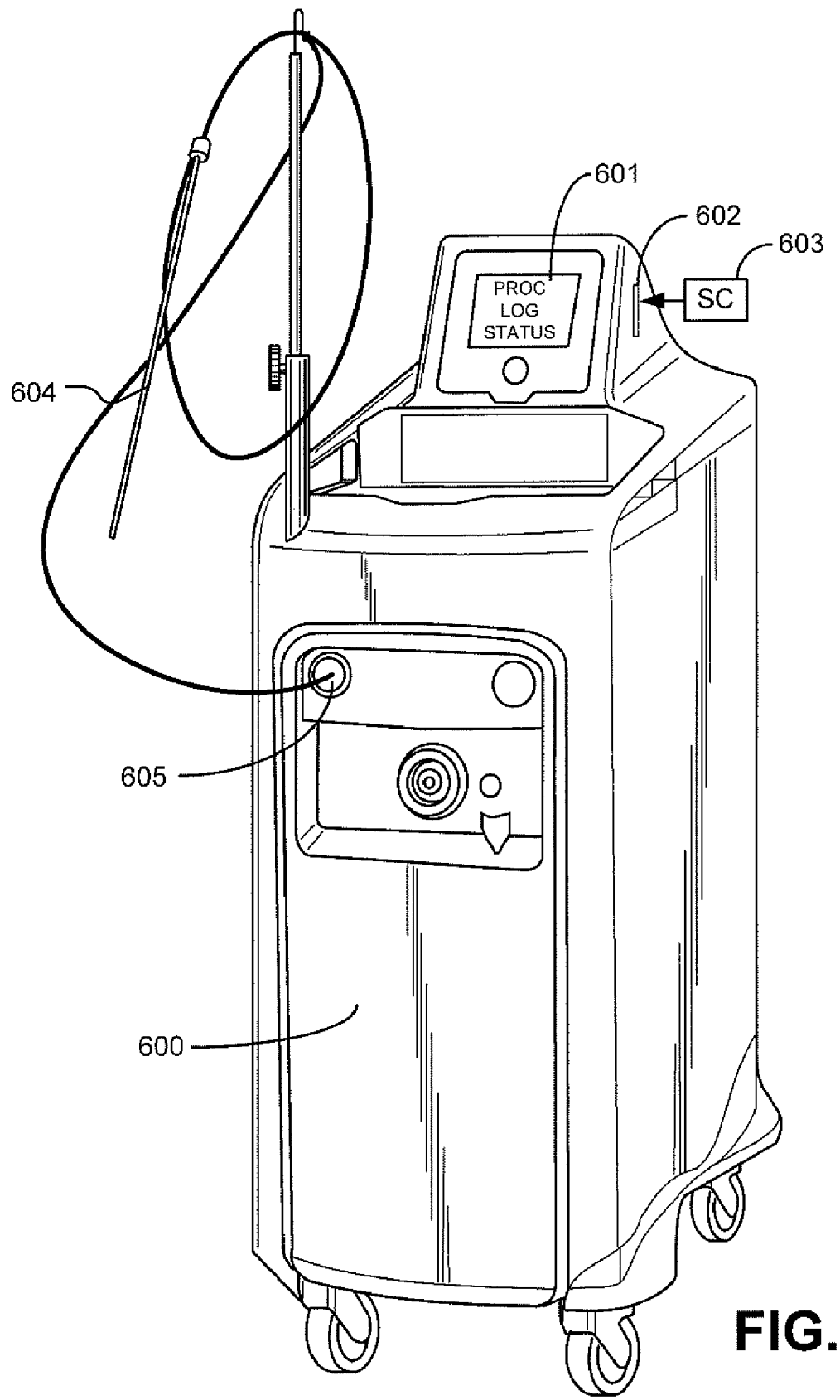
FIG. 6 illustrates a laser system configured as described above, with event logging to a smart card.

FIG. 6 provides a perspective view of a laser unit including a cabinet 600, in which the laser, laser controller and other components are mounted. The laser unit cabinet 600 includes a display 601 which is used for presenting an interactive graphical user interface to an operator during a procedure, including screens for indicating the status of a procedure of logging processes, as illustrated in a simplified manner by the label over the display 601 in FIG. 6. The laser system cabinet 600 includes a slot 602, in which a smart card 603 is inserted, as described above. The fiber optic delivery device 604 includes a coupler 605, which mates with a corresponding coupler on the cabinet 600. The cabinet illustrated, with the exception of the event log status screen, is like that used with a commercially available Green Light PV™ Laser System, mentioned above.

The technology described herein includes a laser system, which is a complex and expensive device, and a kit that includes a fiber optic delivery device and a log configured smartcard. The kit is typically delivered to a user independently of the laser system. The kit is intended for a single use or a controlled number of uses, while the laser system is intended for long-term use. The smart card is separate from the fiber-optic delivery device in embodiments of the kit. In other embodiments, the smart card functionality can be embedded in the coupler 502 or otherwise attached to the fiber-optic delivery device. In embodiments where the smart card is separate or removable, the smart card can be returned to the laser manufacturer or other destination in which the event log data can be used for analysis of the procedures that are executed using the laser system and the fiber optic delivery device. In some systems, it is preferable that delivery device and the smart card be separated, at least after use, because the fiber optic delivery device may comprise a biohazard after use in a procedure. The smart card is uniquely identified with a particular fiber-optic delivery device, making it suitable for accurate and reliable data gathering, even when it is provided separated from the fiber-optic delivery device to the destination at which the event log is analyzed.

The event log, which comprises event codes, timestamps and supporting data, for the sequence of events which occur during a procedure that applies the delivery device, can be used to replay the procedure precisely in time, and step by step. The structure of the smart card, or other portable memory device, is set up so that it can be assured before enabling the laser system that the smartcard is configured for recording the event log. The kit comprising the delivery device and the smart card, which are adapted for use with the laser system, therefore provides a unique data gathering system with assurances that successful accounting for use of the delivery device and the laser system can be gathered. Therefore, reliable data is generated in support of failure analysis for delivery devices, analysis of procedures executed using the delivery devices, and for understanding of patterns of use that can be applied for improving delivery devices and laser systems.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A method for operating a system to perform a procedure that includes a sequence of events, comprising:

detecting the presence of a portable memory device coupled to the system, and reading data on the portable memory device usable to identify an associated delivery device;

reading an identifier for a delivery device coupled to the system;

matching the identifier read from the delivery device with the associated delivery device indicated by data read from the portable memory device;

verifying that the portable memory device includes a data structure adapted for storage of an event log, comprising event codes corresponding to the events in the sequence of events;

enabling a process for delivery of product to the delivery device if said matching and said verifying are successful; and writing an event code, including a time stamp, to the data structure adapted for storage of the event log, to record an event in the sequence of events, and verifying whether the event code and time stamp were successfully written, and if the verifying fails, then disabling the system from providing energy to the delivery device.

2. The method of claim 1, including authenticating the portable memory device.

3. The method of claim 1, including writing event codes, including time stamps, to the data structure adapted for storage of the event log, to record an event in the sequence of events.

4. The method of claim 1, including writing an event code, including a time stamp, to the data structure adapted for storage of the event log, to record an event in the sequence of events, and verifying that the event code and time stamp were successfully written.

5. The method of claim 1, including writing an event code, including a time stamp, to the data structure adapted for storage of the event log, to record an event in the sequence of events, and verifying whether the event code and time stamp were successfully written, and if the verifying fails, then signaling an event log error.

6. The method of claim 1, including writing data to the portable memory device indicating a condition of the system usable for interpretation of data in the event log.

7. The method of claim 1, wherein said system comprises a laser and a data processor controlling the laser, and the delivery device comprises an optical fiber.

* * * * *